(12) United States Patent
Wolff et al.

(10) Patent No.: US 8,084,019 B2
(45) Date of Patent: *Dec. 27, 2011

(54) PERSONAL CARE FIXATIVE

(75) Inventors: Norwin W. Wolff, Marshfield Hills, MA (US); Timothy L. Martin, Louisville, KY (US); Thomas L. Hiff, Strasbourg (FR)

(73) Assignee: Interpolymer Corporation, Canton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/883,820

(22) Filed: Sep. 16, 2010

(65) Prior Publication Data

US 2011/0014146 A1 Jan. 20, 2011

Related U.S. Application Data

(60) Continuation of application No. 12/287,890, filed on Oct. 14, 2008, now Pat. No. 7,824,666, which is a division of application No. 10/591,886, filed as application No. PCT/US2005/007925 on Mar. 8, 2005, now Pat. No. 7,829,071.

(60) Provisional application No. 60/551,658, filed on Mar. 9, 2004, provisional application No. 60/606,985, filed on Sep. 3, 2004, provisional application No. 60/627,224, filed on Nov. 12, 2004.

(51) Int. Cl.
*A61Q 5/06* (2006.01)

(52) U.S. Cl. .......... 424/70.16; 424/47; 424/70.122; 424/70.12; 424/70.15; 525/66; 525/71; 525/191; 528/271; 528/288

(58) Field of Classification Search .......... 424/47, 424/70.122, 70.11, 70.12, 70.15, 70.16, 70.21, 424/70.22, 70.27, 70.28, 70.29, 70.31; 525/66, 525/77, 191, 418; 528/271, 288; 523/124; 524/28; 510/475; 55/528
See application file for complete search history.

(56) References Cited

U.S. PATENT DOCUMENTS

| | | |
|---|---|---|
| 3,145,147 A | 8/1964 | Glickman et al. |
| 3,932,610 A | 1/1976 | Rudy et al. |
| 4,177,178 A | 12/1979 | Das et al. |
| 4,196,190 A | 4/1980 | Gehman et al. |
| 4,223,009 A | 9/1980 | Chakrabarti |
| 4,501,834 A | 2/1985 | Su |
| 4,521,404 A | 6/1985 | Lorenz et al. |
| 4,710,374 A | 12/1987 | Grollier et al. |
| 4,725,492 A | 2/1988 | Yazaki et al. |
| 4,796,646 A | 1/1989 | Grollier et al. |
| 5,009,880 A | 4/1991 | Grollier et al. |
| 5,068,099 A | 11/1991 | Sramek |
| 5,126,124 A | 6/1992 | Tazi et al. |
| 5,185,143 A | 2/1993 | Cohen |
| 5,441,728 A | 8/1995 | Tsaur et al. |
| 5,501,851 A | 3/1996 | Mudge et al. |
| 5,519,063 A | 5/1996 | Mondet et al. |
| 5,686,062 A | 11/1997 | Tong |
| 5,723,113 A | 3/1998 | Faryniarz et al. |
| 5,948,396 A * | 9/1999 | Das et al. .......... 424/70.17 |
| 5,980,878 A | 11/1999 | Torgerson et al. |
| 5,997,851 A | 12/1999 | Cox et al. |
| 5,998,500 A * | 12/1999 | Cahill et al. .......... 523/124 |
| 6,136,296 A | 10/2000 | Midha et al. |
| 6,294,158 B1 | 9/2001 | Dupuis |
| 6,297,326 B1 | 10/2001 | Wang et al. |
| 6,482,394 B1 | 11/2002 | Schehlmann et al. |
| 6,696,050 B2 | 2/2004 | Barbuzzi et al. |
| 2003/0171246 A1 | 9/2003 | Dieter et al. |
| 2003/0180245 A1 | 9/2003 | Gotsche et al. |

FOREIGN PATENT DOCUMENTS

EP 0 581 264 A 2/1994

OTHER PUBLICATIONS

International Search Report for Int'l Application No. PCT/US2005/007925, Date of mailing: Jul. 12, 2005.

* cited by examiner

*Primary Examiner* — James J Seidleck
*Assistant Examiner* — Frances Tischler
(74) *Attorney, Agent, or Firm* — Hamilton, Brook, Smith & Reynolds, P.C.

(57) ABSTRACT

The present invention is directed to bimodal polymer compositions and personal care fixatives containing bimodal polymer compositions. The present invention includes a bimodal polymer composition having a first polymer with anionic character and a second polymer with cationic character and wherein the polymers form an interpenetrating polymer network. In one embodiment, the present invention also includes personal care fixatives (e.g., health care, hygiene or cosmetic compositions) containing the bimodal polymer composition. The present invention also includes methods for forming bimodal polymer compositions.

1 Claim, No Drawings

PERSONAL CARE FIXATIVE

RELATED APPLICATION(S)

This application is a continuation of U.S. application Ser. No. 12/287,890, filed Oct. 14, 2008, now U.S. Pat. No. 7,824,666, which is a divisional of U.S. application Ser. No. 10/591,886 filed on Apr. 26, 2007, now U.S. Pat. No. 7,829,071 which was the U.S. National Stage of International Application No. PCT/US2005/007925, filed Mar. 8, 2005, published as WO 2005/087191 in English, and claims the benefit under 35 U.S.C. §119 or 365 to U.S. Provisional Application No. 60/551,658, filed Mar. 9, 2004; U.S. Provisional Patent Application No. 60/606,985, filed on Sep. 3, 2004; and U.S. Provisional Patent Application No. 60/627,224, filed on Nov. 12, 2004, the entire teachings of all of which are incorporated herein by reference.

BACKGROUND OF THE INVENTION

Recent regulatory legislation and environmental concerns require that personal care fixatives contain lower levels of volatile organic compounds (VOC) than are presently found in many commercially available fixative products. For example, desirable hair fixative compositions should have VOC levels of less than about 55 weight percent and should exhibit little or no loss in curl retention in humidity conditions, good holding power, ease of removal and resistance to build up.

A need exists for a personal care fixative that contains lower levels of volatile organic compounds than the VOC levels found in currently available fixative products while retaining or improving upon the fixative properties of those currently available fixative products.

SUMMARY OF THE INVENTION

The present invention is directed to bimodal polymer compositions and personal care fixatives containing bimodal polymer compositions. The present invention includes a bimodal polymer composition having a first polymer with anionic character and a second polymer with cationic character and wherein the polymers form an interpenetrating polymer network. In one embodiment, the present invention also includes personal care fixatives (e.g., health care, hygiene or cosmetic compositions) containing the bimodal polymer composition.

The present invention also includes methods for forming a bimodal polymer composition. In one embodiment, a method for forming a bimodal polymer composition includes the step of polymerizing monomers to form a first polymer with cationic character in the presence of a second polymer with anionic character. In another embodiment, a method for forming a bimodal polymer composition includes the step of polymerizing monomers to form a first polymer with anionic character in the presence of a second polymer with cationic character.

A method for forming a bimodal polymer composition is also described herein that includes the step of polymerizing monomers to form a first polymer with cationic character in the presence of a second polymer with anionic character wherein the first polymer is formed from a monomer composition including about 35 to about 45 weight percent ammonium derivative monomer, about 15 to about 30 weight percent water insoluble monomer, and about 5 to about 15 weight percent water soluble monomer.

Personal care fixatives containing the present bimodal polymer compositions can contain lower levels of volatile organic compounds than the VOC levels found in currently available fixative products. In addition, the present personal care fixatives can have acceptable, or even improved, fixative properties.

Personal care fixatives containing bimodal polymer compositions of the present invention can gel at relatively low solids concentrations and/or at relatively high humidity conditions. Without being held to any particular theory, the ability of the present fixatives to gel at relatively low solids concentrations and/or at relatively high humidity conditions is thought to be due to ionic bonding of the bimodal polymer composition's polymer constituents. The present personal care fixatives can also gel quickly, allowing fixatives with dilute concentrations of the bimodal polymer composition to hold keratin-type substrates (e.g., hair) while volatile substances contained therein, such as water or alcohol, evaporate. This quick gelling makes the bimodal polymer compositions of the present invention particularly valuable for producing personal care fixatives that contain low VOC concentrations. In addition, ionic cross-linking is thought to produce good adhesion to keratin-type substrates due to an increase in cohesive energy density provided by polar groups contained in the bimodal polymer compositions.

The bimodal polymer compositions of the present invention have acceptable adhesion to keratin-type substances such as hair, skin, fingernails, and toenails. The bimodal compositions described herein can form polymer films with acceptable adhesion in relatively high humidity conditions from personal care fixatives having relatively low concentrations of volatile organic compounds. The polymer films formed from these inventive personal care fixatives can also provide improved film properties, for example, gloss, water resistance, and abrasion resistance, in a variety of personal care applications.

The bimodal polymer compositions of the present invention represent a significant advance over mere blends of polymers. Without being held to any particular theory, it is believed that blends of polymers containing anionic and cationic character can have only very limited stability. Further, it is believed that blends of polymers containing anionic and cationic character are limited in their ability to complex ionically. The bimodal polymer compositions of the present invention can have increased stability over polymer blends. In addition, it is believed that the present bimodal polymer compositions contain ionic moieties (e.g., groups having anionic and cationic functionalities) in close proximity to each other, whereby the polymer chains can interact in a manner generally not possible in a blend of polymers.

DETAILED DESCRIPTION OF THE INVENTION

A description of preferred embodiments of the invention follows.

The present invention is directed to bimodal polymer compositions and personal care fixatives containing bimodal polymer compositions. The present invention includes a bimodal polymer composition having a first polymer with anionic character and a second polymer with cationic character and wherein the polymers form an interpenetrating polymer network.

"Bimodal," as that term is used herein, describes polymer compositions that include two polymers, one having anionic character and one having cationic character.

An "interpenetrating polymer network," as that term is used herein, refers to a polymer structure wherein a monomer has been polymerized in the presence of another polymer. For example, an interpenetrating polymer network is formed by polymerizing a monomer to form the second polymer in the presence of the first polymer. An interpenetrating polymer network contains a polymer homogeneity that generally is not obtained from blending two polymers.

In one embodiment, the first polymer, the second polymer, or both the first and the second polymer of the bimodal polymer composition have a molecular weight of at least about 1,000 daltons, for example, ranging from about 1,000 to about 1,000,000 daltons, e.g., ranging from about 1,000 to about 100,000 daltons or ranging from about 2,000 to about 1,000,000 daltons. In one embodiment, the first polymer has a molecular weight ranging from about 1,000 to about 100,000 daltons and the second polymer has a molecular weight ranging from about 2,000 to about 1,000,000 daltons. In another embodiment, the first polymer has a molecular weight ranging from about 2,000 to about 1,000,000 daltons and the second polymer has a molecular weight ranging from about 1,000 to about 100,000 daltons.

In one embodiment, the first polymer includes the carboxylate salt monomer unit represented by Chemical Structure I:

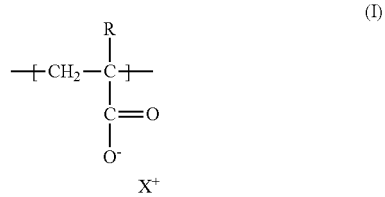

wherein R is hydrogen or an alkyl group and $X^+$ is a salt-forming cation.

An "alkyl group," as the term is used herein, is a hydrocarbon in a molecule that is bonded to one other group in the molecule through a single covalent bond from one of its carbon atoms. Alkyl groups can be cyclic, branched or unbranched, substituted or unsubstituted, and/or saturated or unsaturated. An alkyl group can have, for example, 1 to about 24 carbons atoms, 1 to about 12 carbon atoms, or about 1 to about 4 carbon atoms, e.g., methyl, ethyl, n-propyl, iso-propyl, n-butyl, sec-butyl and tert-butyl.

In one embodiment, the first polymer is the polymer contained in a commercially available SYNTRAN® polymer dispersion. For example, the polymer with anionic character can be the polymer contained in, for example, SYNTRAN® 1501, SYNTRAN® 1555, SYNTRAN® 1560, or in blends thereof. SYNTRAN® is a trademark of Interpolymer Corporation (Canton, Mass.).

SYNTRAN® 1501, SYNTRAN® 1555, and SYNTRAN® 1560 are water-based dispersions of polymers formed of acrylate monomers of the general chemical formula $(\text{—CH}_2\text{—CH(COOR)—})_n$. These water-based dispersions of polymers generally contain about 24 to about 25 weight percent of acrylate copolymer and about 74 to about 75 weight percent water. SYNTRAN® 1501 further contains about 1 weight percent sodium alkylpolyethoxyethanol sulfosuccinate and about 1 weight percent sodium lauryl sulfate. SYNTRAN® 1555 further contains about 1 weight percent sodium lauryl sulfate and about 1 weight percent sodium laurylpolyethoxyethanol. SYNTRAN® 1560 further contains about 1 weight percent sodium alkylpolyethoxyethanol sulfosuccinate, about 1 weight percent sodium lauryl sulfate, and about 1 weight percent sodium laurylpolyethoxyethanol.

The first polymer of the bimodal polymer composition includes, in one embodiment, at least about 10 weight percent of carboxylate salt monomer units. For example, the first polymer can include about 10 to about 20 or about 12 to about 20 weight percent of carboxylate salt monomer units.

In one embodiment, the second polymer includes the cationic monomer unit represented by Chemical Structure II:

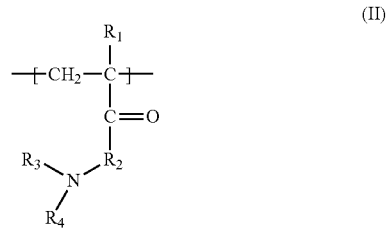

or a quaternized adduct thereof, wherein $R_1$, $R_3$ and $R_4$ are, independently, hydrogen or an alkyl group and $R_2$ is an alkyl group.

In one embodiment, the polymer with cationic character is the polymer contained in a commercially available SYNTRAN® polymer dispersion. For example, the polymer with cationic character can be the polymer contained in, for example, SYNTRAN® FX30. SYNTRAN® FX30 is a water-based dispersion of polymer that includes diethyl amino ethyl methacrylate.

In one embodiment, the second polymer (with cationic character) includes an ammonium derivative monomer unit. The ammonium derivative monomer unit can include, but is not limited to, dialkyl amino alkyl acrylates, dialkyl amino alkyl methacrylates, quaternized adducts of dialkyl amino alkyl acrylate, quaternized adducts of dialkyl amino alkyl methacrylate, methacrylamide and esters thereof, vinyl pyrrolidone and vinyl caprolactam. In one embodiment, the ammonium derivative monomer unit is dimethylaminoethyl methacrylate or a quaternized adduct thereof. The second polymer can contain about 10 to about 90 weight percent of the ammonium derivative monomer unit(s). For example, the second polymer can contain about 20 to about 80, about 30 to about 70, or about 40 to about 60 weight percent ammonium derivative monomer unit(s).

In one embodiment, the second polymer includes a water insoluble monomer unit. The water insoluble monomer unit can include, but is not limited to, esters of acrylate, esters of methacrylate, ethers of acrylate, ethers of methacrylate, styrenes, and alpha-methyl styrene. In one embodiment, the water insoluble monomer unit is butyl methacrylate. The second polymer can contain about 10 to about 90 weight percent of the water insoluble monomer unit(s). For example, the second polymer can contain about 20 to about 80, about 30 to about 70, or about 40 to about 60 weight percent water insoluble monomer unit(s).

The second polymer can also include a water soluble monomer unit. For example, water soluble monomer units can include hydroxy functional acrylates, hydroxy functional methacrylates, and alkoxylated adducts thereof such as ethoxylated and/or propoxylated adducts thereof. In one particular embodiment, the second polymer includes a hydroxypropyl methacrylate monomer unit. The second polymer can contain up to about 80 weight percent of the water soluble monomer unit(s). For example, the second polymer can contain 0 to about 70, about 1 to about 50, about 5 to about 25, or about 10 to about 15 weight percent water insoluble monomer unit(s).

The second polymer can include a cross-linking or multifunctional monomer unit. For example, the second polymer can contain a multifunctional acrylate, a multifunctional methacrylate, diallyl phthalate, or any other cross-linking or multifunctional monomer units known in the art. The second polymer can contain up to about 10 weight percent of the cross-linking or multifunctional monomer unit(s). For example, the second polymer can contain 0 to about 10 such as about 1 to about 5 or about 5 to about 10 weight percent cross-linking or multifunctional monomer unit monomer unit(s).

In some embodiments, the second polymer can include a monomer unit of anionic functionality such as, but not limited to, acrylic acid, methacrylic acid and esters thereof.

In specific embodiments, the second polymer includes an ammonium derivative monomer unit, a water insoluble monomer unit, and optionally, a water soluble monomer unit (e.g., hydroxy functional acrylates, hydroxy functional methacrylates, and alkoxylated adducts thereof) and/or a cross-linking or multifunctional monomer unit. For example, the second polymer can include about 10 to about 90 weight percent of an ammonium derivative monomer unit, about 10 to about 90 weight percent of a water insoluble monomer unit, and optionally, up to about 80 weight percent of a water soluble monomer unit (e.g., hydroxy functional acrylates, hydroxy functional methacrylates, and alkoxylated adducts thereof) and/or up to about 10 weight percent of a cross-linking or multifunctional monomer unit. In one particular embodiment, the second polymer includes about 55 to about 65 weight percent of dialkyl amino alkyl methacrylate, about 25 to about 35 weight percent of alkyl methacrylate, and about 5 to about 15 weight percent of hydroxy functional methacrylate. For example, the second polymer can include about 55 to about 65 weight percent of dimethylaminoethyl methacrylate, about 25 to about 35 weight percent of butyl methacrylate, and about 5 to about 15 weight percent of hydroxypropyl methacrylate.

In one embodiment, the first polymer is the polymer contained in SYNTRAN® 1501, SYNTRAN® 1555, SYNTRAN® 1560, or in blends thereof and the second polymer includes an ammonium derivative monomer unit, a water insoluble monomer unit, and optionally, a water soluble monomer unit and/or a cross-linking or multifunctional monomer unit, as described supra. The first polymer (e.g., the polymer of SYNTRAN® 1501, SYNTRAN® 1555, SYNTRAN® 1560, or of blends thereof) can be present in the bimodal polymer composition in a concentration of up about 90 weight percent, for example, about 10 to about 90, about 20 to about 80, about 30 to about 70, or about 40 to about 60 weight percent. In one embodiment, the first polymer can be present in the bimodal polymer composition in a concentration of about 10 to about 30 weight percent such as about 15 to about 25 weight percent. The second polymer can be present in the bimodal polymer composition in a concentration of up to about 90 weight percent, for example, about 10 to about 90, about 20 to about 80, about 30 to about 70, or about 40 to about 60 weight percent. In one embodiment, the second polymer can be present in the bimodal polymer composition in a concentration of about 1 to about 30 weight percent such as about 5 to about 20 weight percent.

In one embodiment, the first polymer (with anionic character) includes a monomer unit with anionic functionality. The monomer unit with anionic functionality can include, but is not limited to, acidic acrylate monomer, acidic methacrylate monomer, 2-sulfoethylmethacrylate and salts thereof, 2-acrylamido-2-methyl propanesulfonate and salts thereof, crotonic acid, itaonic acid, fumaric acid, acid anhydrides, and half esters of di-carboxylate monomer. The first polymer can contain about 10 to about 90 weight percent of monomer unit(s) with anionic functionality. For example, the second polymer can contain about 20 to about 80, about 30 to about 70, or about 40 to about 60 weight percent monomer unit(s) with anionic functionality.

In one embodiment, the first polymer includes a water insoluble monomer unit. The water insoluble monomer unit can include, but is not limited to, esters of acrylate, esters of methacrylate, ethers of acrylate, ethers of methacrylate, styrenes, and alpha-methyl styrene. The first polymer can contain about 10 to about 90 weight percent of the water insoluble monomer unit(s). For example, the first polymer can contain about 20 to about 80, about 30 to about 70, or about 40 to about 60 weight percent water insoluble monomer unit(s).

The first polymer can also include a water soluble monomer unit. For example, water soluble monomers can include hydroxy functional acrylates, hydroxy functional methacrylates, and alkoxylated adducts thereof such as ethoxylated and/or propoxylated adducts thereof. The first polymer can contain up to about 80 weight percent of the water soluble monomer unit(s). For example, the first polymer can contain 0 to about 70, about 1 to about 50, about 5 to about 25, or about 10 to about 15 weight percent water insoluble monomer unit(s).

The first polymer can include a cross-linking or multifunctional monomer unit. For example, the first polymer can contain a multifunctional acrylate, a multifunctional methacrylate, diallyl phthalate, or any other cross-linking or multifunctional monomer units known in the art. The first polymer can contain up to about 10 weight percent of the cross-linking or multifunctional monomer unit(s). For example, the first polymer can contain 0 to about 10 such as about 1 to about 5 or about 5 to about 10 weight percent cross-linking or multifunctional monomer unit monomer unit(s). In one embodiment, the first polymer also includes a chain modifier. Chain modifiers are known in the art and include, but are not limited to, alcohols and mercaptans.

In specific embodiments, the first polymer includes a monomer unit with anionic functionality, a water insoluble monomer unit, and optionally, a water soluble monomer unit (e.g., hydroxy functional acrylates, hydroxy functional methacrylates, and alkoxylated adducts thereof) and/or a cross-linking or multifunctional monomer unit. For example, the first polymer can include about 10 to about 90 weight percent of a monomer unit with anionic functionality, about 10 to about 90 weight percent of a water insoluble monomer unit, and optionally, up to about 80 weight percent of a water soluble monomer unit (e.g., hydroxy functional acrylates, hydroxy functional methacrylates, and alkoxylated adducts thereof) and/or up to about 10 weight percent of a cross-linking or multifunctional monomer unit.

In one embodiment, the first polymer includes a monomer unit with anionic functionality, a water insoluble monomer unit, and optionally, a water soluble monomer unit and/or a cross-linking or multifunctional monomer unit, as described supra, and the second polymer is the polymer contained in SYNTRAN® FX30. The first polymer can be present in the bimodal polymer composition in a concentration of up to about 90 weight percent, for example, about 10 to about 90, about 20 to about 80, about 30 to about 70, or about 40 to about 60 weight percent. In one embodiment, the first polymer can be present in the bimodal polymer composition in a concentration of about 1 to about 30 weight percent such as about 5 to about 20 weight percent. The second polymer (e.g., the polymer of SYNTRAN® FX30) can be present in the bimodal polymer composition in a concentration of up about 90 weight percent, for example, about 10 to about 90, about 20 to about 80, about 30 to about 70, or about 40 to about 60 weight percent. In one embodiment, the second polymer can be present in the bimodal polymer composition in a concentration of about 10 to about 30 weight percent such as about 15 to about 25 weight percent.

In some embodiments, substantially all or all or the carboxylate groups of a constituent polymer of the bimodal polymer composition have been neutralized, e.g., as salts. Neutralization can be accomplished by techniques known in the art, for example, carboxylic acid groups of the polymer can be reacted with one or more alkaline reagents. For example, in one embodiment, the first polymer, with anionic character, contains carboxylate groups that have been neutralized, for example, by forming carboxylate salts.

In one embodiment, the present bimodal polymer composition includes at least about 10 weight percent of monomer units with anionic functionality. For example, the bimodal polymer composition can include at least about 20 or at least about 30 weight percent monomer units with anionic functionality. Additionally, the bimodal polymer composition can include at least about 10 weight percent of monomer units with cationic functionality. For example, the bimodal polymer composition can include at least about 20 or at least about 30 weight percent monomer units with cationic functionality.

In one specific embodiment, the bimodal polymer composition can contain less than about 40 weight percent hydroxyl-containing monomer units. For example, the bimodal polymer composition can contain less than about 30 or less than about 20 weight percent hydroxyl-containing monomer units.

In one embodiment, the glass transition temperature ($T_g$) of the present bimodal polymer compositions can be indicative of the bimodal nature of the compositions. The glass transition temperature of the present bimodal polymer compositions can be less than about 60° C. such as less than about 30° C.

The present invention also includes methods for forming a bimodal polymer composition. The method can include the step of polymerizing monomers to form a first polymer with cationic character in the presence of a second polymer with anionic character. In one embodiment, the second polymer is represented by Chemical Structure I, supra. For example, the second polymer is represented by Chemical Structure I wherein R is hydrogen.

In one embodiment, the bimodal polymer composition is formed by the free radical polymerization of the first polymer monomer components in the presence of the second polymer. For example, the bimodal polymer composition is formed by the free radical polymerization of an ammonium derivative monomer unit, a water insoluble monomer unit, and optionally, a water soluble monomer unit (e.g., hydroxy functional acrylates, hydroxy functional methacrylates, and alkoxylated adducts thereof) and/or a cross-linking or multifunctional monomer unit in the presence of the second polymer (e.g., the polymer contained in SYNTRAN® 1501, SYNTRAN® 1555, SYNTRAN® 1560, and blends thereof).

In one embodiment, the second polymer is dispersed in an aqueous medium. The aqueous medium can further include, for example, salts of alkylpolyethoxyethanol sulfosuccinate, salts of lauryl sulfate, and salts of laurylpolyethoxyethanol. In one embodiment, the concentration of the second polymer in the aqueous medium is about 10 to about 40 weight percent such as about 20 to about 30 weight percent or about 24 to about 25 weight percent. For example, water-dispersed polymers can be used such as, but not limited to, SYNTRAN® 1501, SYNTRAN® 1555, SYNTRAN® 1560, and blends thereof.

The reaction of this above-described monomer composition can be moved to complete, or substantially complete, conversion by conventional methods known in the art, e.g., by emulsion polymerization, in water, solvent, or a combination thereof. The bimodal polymer composition thus obtained can be neutralized with an appropriate organic base or inorganic base to 0 to about 100 percent of the available carboxyl groups.

In another embodiment, a method forming a bimodal polymer composition includes the step of polymerizing monomers to form a first polymer with anionic character in the presence of a second polymer with cationic character. In one embodiment, the second polymer is represented by Chemical Structure II, supra, such as diethylaminoethyl methacrylate or a quaternized adduct thereof. The bimodal polymer composition can be formed by the free radical polymerization of the first polymer monomer components in the presence of the second polymer. For example, the bimodal polymer composition is formed by the free radical polymerization of a monomer unit with anionic functionality, a water insoluble monomer unit, and optionally, a water soluble monomer unit (e.g., hydroxy functional acrylates, hydroxy functional methacrylates, and alkoxylated adducts thereof) and/or a cross-linking or multifunctional monomer unit in the presence of the second polymer (e.g., SYNTRAN® FX30 and the like).

In one embodiment, the second polymer is dispersed in an aqueous medium. The aqueous medium can further include, for example, salts of alkylpolyethoxyethanol sulfosuccinate, salts of lauryl sulfate, and salts of laurylpolyethoxyethanol. In one embodiment, the concentration of the second polymer in the aqueous medium is about 10 to about 40 weight percent such as about 20 to about 30 weight percent or about 24 to about 25 weight percent. For example, a water-dispersed polymer can be used such as, but not limited to, SYNTRAN® FX30.

The reaction of this above-described monomer composition can be moved to complete, or substantially complete, conversion by conventional methods known in the art, e.g., by emulsion polymerization, in water, solvent, or a combination thereof. The bimodal polymer composition thus obtained can be neutralized with an appropriate organic acid or inorganic acid to 0 to about 100 percent of the available amino groups.

General techniques associated with emulsion polymerization suitable for forming the vehicle composition of this invention are discussed in D. C. Blackley, Emulsion Polymerization (Wiley, 1975). The teachings of which are incorporated herein by reference in their entirety. Final pH can be adjusted with a suitable cosmetically acceptable base used in the cosmetic industry. If the polymer is associated with other non-cosmetic applications, other more aggressive bases may be incorporated.

The present invention also includes the bimodal polymer compositions produced by the methods described herein. In one aspect, the invention includes personal care fixatives that include bimodal polymer compositions produced by the methods described herein.

The bimodal polymer compositions of the present invention can be used in personal care products such as personal care fixatives. For example, the bimodal polymer compositions can be used in hair fixatives such as, but not limited to, sprays, gels and mousses. In one embodiment, the invention includes a fixative composition such as a personal care fixative. The personal care fixative can include the bimodal polymer composition and a cosmetically acceptable medium. The cosmetically acceptable medium can include one or more relatively volatile solvents such as water or an alcohol. The personal care fixative can include a total volatile solvent concentration ranging from about 25 to about 95 weight percent or more, e.g., about 30 to about 95, about 50 to about 95, or about 75 to about 95 weight percent total volatile solvents. In one embodiment, the cosmetically acceptable medium is principally water by weight. In some embodiments, the personal care fixative is at least about 20, 30, 40, 50, 60, 70, 80, or at least about 90 weight percent water. In addition, in some embodiments, the cosmetically acceptable medium also includes an alcohol such as ethanol or panthenol. Preferably, the concentration of volatile organic compounds (VOC) such as, for example, alcohol is less than about 55 weight percent. For example the VOC concentration can be less than about 50, 45, 40, 35, 30, 25, 20, 15, 10, or less than 5 weight percent VOC. The personal care fixative can also contain any of the personal care fixative additives known to those of skill in the art. For example, the personal care fixative further can contain at least one component selected from the group consisting of thickening agents, dispersing agents, emulsifiers, emollients, stabilizers, surfactants, fragrances, preservatives, proteins, conditioners, colorants, dyes, plasticizers, neutralizers, glossifiers and propellants.

Application of the personal care fixatives described herein to a subject (e.g., to a human subject) typically produces a polymer film. The polymer film can be principally composed of the bimodal polymer composition. In one embodiment, the polymer film is easily removed using normal hygiene procedures. For example, the polymer film can be water soluble or water dispersible. In one embodiment, the polymer film is removeable by water and soap or shampoo.

In some embodiments, the bimodal polymer compositions of the present invention can be used in personal care products also containing water based olefin, styrene and/or acrylic polymer systems such as described in, for example, U.S. Provisional Patent Application No. 60/606,985 by Wolff, et al., filed on Sep. 3, 2004, and in U.S. Provisional Patent Application No. 60/627,224 by Wolff, et al., filed on Nov. 12, 2004, the entire teachings of both of which are incorporated herein by reference. For example, in one embodiment, the personal care product can contain an olefin graft polymer such as SYNTRAN® Olefin Graft PC 5208 (Interpolymer Corp., Canton, Mass.). In some embodiments, the personal care product can contain an olefin graft polymer in a concentration of about 10 to about 90 percent by polymer weight and a bimodal polymer composition concentration of about 90 to about 10 percent by polymer weight. For example, the personal care product can contain an olefin graft polymer in a concentration of about 20 to about 80 percent by polymer weight and a bimodal polymer composition concentration of about 80 to about 20 percent by polymer weight.

EXEMPLIFICATION

The invention will now be further and specifically described by the following examples which are not intended to be limiting.

Example 1

This example describes the production of a bimodal polymer composition.

Into a 1000 ml resin flask equipped with an agitator, condensers, and addition ports, 500 grams SYNTRAN® 1501 (containing 25 weight percent non-volatiles) was added. The SYNTRAN® 1501 was heated to 80° C. slowly with a water bath and keeping the flask blanketed with an inert gas. When the temperature was reached, a premix of 40 grams of water and 0.5 gram of ammonium persulfate was slowly added.

Immediately following, the following premix was added: 16 grams dimethylaminoethyl methacrylate, 8 grams butyl methacrylate, 3 grams hydroxypropyl methacrylate, 7 grams water, and 0.5 gram C12-C15 alkyl alcohol ethoxylate/10 mole. The reaction was allowed to exotherm and the temperature was kept between about 80° C. and about 85° C. using the water bath. The temperature was held for two hours, then 30 grams water, 0.2 gram ammonium bisulfite (45% solution), and 0.5 gram aqua ammonia (28%) were added. The mixture was then held for an additional hour.

Example 2

This example describes the production of a bimodal polymer composition.

Into a 1000 ml resin flask equipped with an agitator, condensers, and addition ports, 350 grams SYNTRAN® 1501 (containing 25 weight percent non-volatiles) and 104 grams of water was added. The SYNTRAN® 1501 was heated to 60° C. slowly with a water bath and keeping the flask blanketed with an inert gas. A slow, even agitation was maintained while the material was in the flask. When the temperature was reached, a premix of 40 grams of water and 0.5 gram of ammonium persulfate was slowly added.

Immediately following, the following premix was added: 25 grams dimethylaminoethyl methacrylate, 30 grams butyl acrylate, 10 grams hydroxyethyl acrylate, 15 grams water, and 1 gram C12-C15 alkyl alcohol ethoxylate/10 mole. The reaction was allowed to exotherm and the temperature was kept between about 80° C. and about 85° C. using the water bath. The temperature was held for two hours, then 40 grams water, 0.2 gram ammonium bisulfite (45% solution), and 0.5 gram aqua ammonia (28%) were added. The mixture was then held for an additional hour.

Example 3

This example describes the preparation of mousse and gel fixatives.
Preparation of Fixatives Mousse and gel fixatives were prepared having the components listed in Tables 1 and 2. (DOW CORNING® is a trademark of Dow Corning (Midland, Mich.). MACKSTAT® is a trademark of The McIntyre Group Ltd. (University Park, Ill.). BRIJ® is a trademark of ICI Americas, Inc. (Wilmington, Del.).)

The bimodal polymer composition used in Mousse Fixative A and the Gel Fixative was produced as described in Example 1. The bimodal polymer composition used in Mousse Fixative B was produced as described in Example 2.

TABLE 1

Gel Fixative

| Component | Supplier | Concentration (weight percent) | Weight (grams) |
| --- | --- | --- | --- |
| Phase A | | | |
| Distilled Water | | 72.68 | 218 |
| Acritimer 940 (carbomer) | Rita Corp. (Woodstock, IL) | 0.60 | 1.80 |
| Triethanolamine (TEA) 99% | Pride Solvents & Chemical Co. (Holtsville, NY) | 0.62 | 1.86 |
| Phase B | | | |
| Bimodal Polymer Composition | | 15 | 45 |
| Phase C | | | |
| Distilled Water | | 10 | 30 |
| DOW CORNING ® 193 Fluid (silicon fluid) | Dow Corning (Midland, MI) | 0.05 | 0.15 |
| Ritapan DL (panthenol) | Rita Corp. (Woodstock, IL) | 0.10 | 0.30 |
| Promois WG (hydrolyzed wheat protein) | Rita Corp. (Woodstock, IL) | 0.05 | 0.15 |
| Promois WG-SIG (hydrolyzed wheat protein PG-Propyl Methylsilanediol) | Rita Corp. (Woodstock, IL) | 0.05 | 0.15 |
| MACKSTAT ® DM-LO (DMDM Hydantoin) | The McIntyre Group Ltd. (University Park, IL) | 0.40 | 1.20 |
| Phase D | | | |
| BRIJ ® 98 Veg (Oleth-20) | Uniqema (New Castle, DE) | 0.35 | 1.05 |
| Fragrance #98444 | Intarome (Norwood, NJ) | 0.1 | 0.30 |
| Total: | | 100 | 300 |

The Gel Fixative, having a composition as shown in Table 1, was prepared by mixing Phase A components. Separately, Phase C and D were mixed. Phases C and D were then warmed and then Phase D was added to Phase C. Phases C and D were then stirred until the mixture was homogeneous. The mixture of Phases C and D were then added to Phase A and stirred. Finally, Phase B was added to the mixture of Phases A, C and D and the resulting mixture was stirred until homogeneous.

TABLE 2

Mousse Fixatives A and B

| Component | Supplier | Concentration (weight percent) | Weight (grams) |
| --- | --- | --- | --- |
| Phase A | | | |
| Distilled Water | | 87.95 | 263.85 |
| Ritapan DL (panthenol) | Rita Corp. (Woodstock, IL) | 0.50 | 1.50 |
| DOW CORNING ® 193 Fluid (silicon fluid) | Dow Corning (Midland, MI) | 0.50 | 1.50 |
| Bimodal Polymer Composition | | 10 | 30 |
| MACKSTAT ® DM-LO (DMDM Hydantoin) | The McIntyre Group Ltd. (University Park, IL) | 0.40 | 1.20 |
| Promois WG (hydrolyzed wheat protein) | Rita Corp. (Woodstock, IL) | 0.10 | 0.30 |
| Promois WG-SIG (hydrolyzed wheat protein PG-Propyl Methylsilanediol) | Rita Corp. (Woodstock, IL) | 0.10 | 0.30 |
| Phase B | | | |
| PEG-40 Hydrogenated Castor Oil | Lipo Chemicals, Inc. (Paterson, NJ) | 0.05 | 0.15 |
| Fragrance # 98444 | Intarome (Norwood, NJ) | 0.10 | 0.30 |
| Polysorbate 20 (PEG-10 Sorbitan Laurate) | Lipo Chemicals, Inc. (Paterson, NJ) | 0.30 | 0.90 |
| Total: | | 100 | 300 |

Mousse Fixatives A and B, having compositions as shown in Table 2, were prepared by adding together Phase A components in the listed order followed by stirring until Phase A was homogeneous. Phase B was then prepared by mixing the listed components. Phase B was added to Phase A and the mixture was stirred until homogeneous.

Evaluation of Fixative Compositions

Several 24 cm tresses of European Brown hair (from same lot of hair) were prepared. Each tress weighed about 6.5 grams. Each tress was washed thoroughly with a strong detergent to remove any residual materials and excess water was removed.

Mousse Application

About 0.5 grams of mousse fixative was applied to each of a set of tresses and was gently spread through the hair. The tips of the hair were then rolled about a ¾ inch to 1 inch curling rod. The tresses were clamped to the curling rods and dried for about five days in air at room temperature.

Gel Application

About 0.8 grams of the gel fixative was applied to each of a set of tresses and was gently spread through the tresses. Each tress was then combed through tress once with fine end of a comb to distribute the gel fixative composition. The tips of the hair were then rolled about a ¾ inch to 1 inch curling rod. The tresses were clamped to the curling rods and dried for about 5 days in air at room temperature.

The dry hair was removed from the curling rods and hung on calibrated boards. The length of the curl was measured. The curled hair was placed in a humidity chamber and position of bottom of curl was noted at prescribed time intervals. The humidity chamber had an average temperature of 82.7° F. and an average humidity of 96.7 percent relative humidity. Table 3 shows the percent curl retention for the Gel Fixative, Mousse Fixatives A and B, and 3 comparative fixatives (CARBOPOL® Polymer Gel, PVP K90 Mousse, and PVP K30 Mousse). The comparative fixatives were prepared by substituting a CARBOPOL® polymer, polyvinyl pyrrlidone (PVP) K90 and PVP K30, respectively, for the bimodal polymer composition in the gel and mousse formulations of Tables 1 and 2. CARBOPOL® is a trademark of Noveon IP Holdings Corp. (Cleveland, Ohio). The PVP K90 and PVP K30 were obtained from ISP Technologies, Inc. (Wayne, N.J.).

Example 4

This example describes three hair fixative compositions.

| Pump Composition A - (Crisp Character) (5% non-volatiles) | |
|---|---|
| bimodal polymer composition | 20 grams (g) |
| water | 24.6 g |
| amino methyl propanol (AMP) | 0.4 g |
| ethyl alcohol, denatured (SDA-40) | 55 g |

The water, SDA-40 and AMP are mixed and the bimodal polymer composition is slowly added with good agitation until dispersed.

| Pump Composition B - (Flexible Hold) (5% non-volatiles) | |
|---|---|
| bimodal polymer composition | 20 grams (g) |
| water | 23.3 g |
| amino methyl propanol (AMP) | 0.5 g |
| Crovol PK-70 | 0.4 g |
| (Croda, Inc., Parsippany, NJ) | |
| DOW CORNING ® 190 Fluid | 0.4 g |
| (Dow Corning Midland, MI) | |
| 1,3-butylene glycol | 0.4 g |
| ethyl alcohol, denatured (SDA-40) | 55.0 g |

All ingredients except for the bimodal polymer composition are mixed with good agitation. The bimodal polymer composition is then added to the mixture with continued agitation.

| Pump Composition C - (Low Static) (5% non-volatiles) | |
|---|---|
| bimodal polymer composition | 14.4 grams (g) |
| water | 21.9 g |
| amino methyl propanol (AMP) | 0.5 g |
| Crovol PK-70 | 0.8 g |
| (Croda, Inc., Parsippany, NJ) | |
| DOW CORNING ® 190 Fluid | 1.2 g |
| (Dow Corning Midland, MI) | |
| panthenol | 0.8 g |
| ethyl alcohol, denatured (SDA-40) | 55 g |
| Statran 1705 | 1.2 g |
| (Interpolymer Corp, Canton, MA) | |

TABLE 3

Hair Curl Retention Using Various Fixatives

| | Gel Fixative | CARBOPOL ® Polymer Gel | PVP K90 Mousse | Mouse Fixative A | PVP K30 Mousse | Mouse Fixative B |
|---|---|---|---|---|---|---|
| Initial Curl Length (cm) | 4.4 | 4.5 | 4.0 | 4.0 | 3.7 | 4.5 |
| Final Curl Length (cm) | 6.5 | 15.3 | 12.1 | 4.7 | 16.0 | 6.5 |
| Time (hours) | Curl Retention Percentage: | | | | | |
| 1 | 96.9 | 97.4 | 96.0 | 100 | 81.3 | 92.8 |
| 2 | 94.4 | 66.7 | 96.5 | 100 | 64 | 92.3 |
| 3 | 89.8 | 48.7 | 73.5 | 96.5 | 46.8 | 89.7 |
| 4 | 89.8 | 44.6 | 65 | 96.5 | 41.9 | 89.7 |
| 5 | 89.3 | 44.6 | 59.5 | 96.5 | 39.4 | 89.7 |

All of the ingredients are mixed with good agitation except the bimodal polymer composition and Statran 1705. The Statran 1705 is slowly added and allowed to mix. After the Statran 1705 is dispersed, the bimodal polymer composition is slowly added and agitated until dispersed.

Example 5

This example describes the production of a bimodal polymer composition.
Into a 1000 ml resin flask equipped with an agitator, condensers, and addition ports, the following was added:

| | |
|---|---|
| Water | 293 grams (g) |
| Sodium lauryl sulfate (30%) | 2.4 g |
| Sodium Alkylpolyethoxyethanol sulfosuccinate | 1.8 g |

This was heated via water bath and under inert gas to 80° C. With good agitation the following was added over a one hour period:

| | |
|---|---|
| Butyl Acrylate | 11.6 g |
| Ethyl Acrylate | 46.7 g |
| Methyl Methacryalte | 29.2 g |
| Methacrylic Acid | 22.1 g |
| Styrene | 7.0 g |

After the mixture had agitated for 15 minutes, a premix of 0.5 grams of ammonium persulfate in 40 grams of water was added followed by 0.2 grams of ammonium bisufite solution (45%). The reaction was allowed to proceed and the temperature was maintained below 80° C. The mixture was held for two hours at the peak temperature. The following was added at this time:

| | |
|---|---|
| Water | 26 g |
| Aqua Ammonia 28% | 13 g |

This was mixed until it became uniform in appearance.
A second mixture of ammonium persulfate, 0.5 grams in 40 grams of water was added and immediately followed with:

| | |
|---|---|
| Dimethylaminoethyl methacrylate | 15.5 g |
| Ethyl Acrylate | 7.8 g |
| Methyl Methacrylate | 15.5 g |

The mixture was allowed to exotherm and was held between 80 and 85° C. for two hours. The mixture was then cooled and filtered.

Example 6

This example describes the preparation of a Texturizing Shampoo.
A Texturizing Shampoo was prepared having the components listed in Table 4. DISSOLVINE—is a trademark of Akzo Nobel (Chicago, Ill.), RITAPAN is a trademark of RITA Corp. (Woodstock, Ill.), MACKADET—is a trademark of The McIntyre Group Ltd. (University Park, Ill.), GERMALL—is a trademark of the ISP Corp. (Wayne, N.J.).

TABLE 4

| Texturizing Shampoo | | | |
|---|---|---|---|
| Component | Supplier | Concentration (weight percent) | Weight (grams) |
| Phase A | | | |
| Distilled Water | | 42.93 | 128.79 |
| DISSOLVINE-$Na_2S$ | Akzo Nobel (Chicago, IL) | 0.10 | 0.30 |
| Ritapan DL | Rita Corp. (Woodstock, IL) | 0.50 | 1.50 |
| Phase B | | | |
| SYNTRAN-Olefin Graft PC 5208 | Interpolymer Corp. (Canton, MA) | 8.00 | 24.00 |
| SYNTRAN-Bimodal PC 5100 | Interpolymer Corp. (Canton, MA) | 2.00 | 6.00 |
| Phase C | | | |
| MACKADET-APB | The McIntyre Group Ltd. (University Park, IL) | 45.00 | 135.00 |
| Phase D | | | |
| GERMALL-Plus | ISP Corp. (Wayne, NJ) | 0.35 | 1.05 |
| Fragrance | Carrubba Inc. (Milford, CT) | 0.30 | 0.90 |
| Citric Acid | | 0.02 | 0.06 |
| Sodium Chloride | | 0.80 | 2.40 |
| Sodium Chloride (viscosity adjustment) | | | 0.30 |
| Total: | | 100 | 300 |

The Texturizing Shampoo, having a composition as shown in Table 4, was prepared by heating water to 45° C. to 50° C. and mixing Phase A components. Separately Phase B was added at 45° C. to Phase A. Then, Phase C was added at 45° C. Finally, Phase D was added to the mixture of Phases A, B and C at 35° C. and the resulting mixture was stirred until homogenous.

Example 7

This example describes the preparation of a 35% VOC Hair Spray.
The 35% VOC Hair Spray was prepared having the components listed in Table 5. AMP-95—is a trademark of Angus Corp. (Chicago, Ill.), DOW CORNING—is a trademark of Dow Corning (Midland, Mich.), CROVOL is a trademark of Croda Inc. (Parsippany, N.J.).

TABLE 5

Low VOC Hair Spray

| Component | Supplier | Concentration (weight percent) | Weight (grams) |
|---|---|---|---|
| Phase A | | | |
| SDA-40B 200 Proof | | 70.00 | 210.00 |
| AMP-95- | Angus Corp. (Chicago, IL) | 0.50 | 1.50 |
| DC 193 Fluid | Dow Corning (Midland, MI) | 0.10 | 0.30 |
| Crovol PK-70 | Croda Inc. (Parsippany, NJ) | 0.05 | 0.15 |
| Phase B | | | |
| SYNTRAN-KL-219C | Interpolymer Corp. (Canton, MA) | 10.00 | 30.00 |
| SYNTRAN-EX 107-21-3 | Interpolymer Corp. (Canton, MA) | 19.35 | 58.05 |
| AMP-95- | Angus Corp. (Chicago, IL) | Sufficient quantity to adjust pH to 8.5-8.7 | |
| Total (100% Concentration): | | 100 | 300 |
| Hair Spray Formulation: | | | |
| 35% VOC Concentrate | | 50% | |
| Propellant | | 50% | |

The 35% VOC Hair Spray, having a composition as shown in Table 5, was prepared by mixing Phase A components and stirring between each component until homogenous. Phase B ingredients were separately added as listed, stirring between each ingredient until homogenous. Phase B was added to Phase A and the mixture was stirred until homogenous.

The low VOC hair spray had the following average particle size:
Valve specification: 020 MB Conclave Kosmos, o18 S90 Stem, 025×013 VT S90
Average Particle Size: 30.18 microns While this invention has been particularly shown and described with references to preferred embodiments thereof, it will be understood by those skilled in the art that various changes in form and details may be made therein without departing from the scope of the invention encompassed by the appended claims.

What is claimed is:

1. A method for forming a bimodal polymer composition, comprising the step of polymerizing monomers to form a first polymer having a first ionic character, in the presence of a second polymer having a second ionic character, and further in the presence of aqueous ammonia,
    wherein said first polymer has a molecular weight ranging from about 1,000 daltons to about 1,000,000 daltons,
    wherein said second polymer has a molecular weight ranging from about 1,000 daltons to about 1,000,000 daltons,
    wherein the first and the second polymers form an interpenetrating polymer network, and
    wherein the second polymer includes dimethyl amino ethyl methacrylate or a quaternized adduct thereof.

* * * * *